US011903637B2

(12) United States Patent
Herbst et al.

(10) Patent No.: US 11,903,637 B2
(45) Date of Patent: Feb. 20, 2024

(54) BLADDER TREATMENT BY ABLATIVE DENERVATION (71) Applicant: Boston Scientific Scimed, Inc., Maple Grove, MN (US)

(72) Inventors: Thomas John Herbst, Coon Rapids, MN (US); Mark W. Boden, Harrisville, RI (US); Sandra Nagale, Bolton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 725 days.

(21) Appl. No.: 16/890,395

(22) Filed: Jun. 2, 2020

(65) Prior Publication Data
US 2020/0297409 A1 Sep. 24, 2020

Related U.S. Application Data (63) Continuation of application No. 14/815,392, filed on Jul. 31, 2015, now abandoned.

(60) Provisional application No. 62/031,584, filed on Jul. 31, 2014.

(51) Int. Cl.
| *A61B 18/14* | (2006.01) |
| *A61B 18/02* | (2006.01) |
| *A61B 18/00* | (2006.01) |
| *A61B 18/18* | (2006.01) |
| *A61B 18/20* | (2006.01) |
| *A61N 7/02* | (2006.01) |

(52) U.S. Cl.
CPC ...... *A61B 18/1485* (2013.01); *A61B 18/1477* (2013.01); *A61B 18/1492* (2013.01); *A61B 18/1815* (2013.01); *A61B 18/20* (2013.01); *A61B 2018/00434* (2013.01); *A61B 2018/00517* (2013.01); *A61B 2018/00577* (2013.01); *A61B 2018/00595* (2013.01); *A61B 2018/0293* (2013.01); *A61B 2018/143* (2013.01); *A61B 2018/1432* (2013.01); *A61B 2018/1475* (2013.01); *A61N 7/022* (2013.01); *A61N 2007/025* (2013.01)

(58) Field of Classification Search
CPC ............ A61B 18/1492; A61B 18/1485; A61B 18/1477
See application file for complete search history.

(56) References Cited

U.S. PATENT DOCUMENTS

| 2004/0199179 A1 | 10/2004 | Elliott |
| 2008/0255553 A1 | 10/2008 | Young et al. |
| 2011/0077644 A1 | 3/2011 | Pham et al. |

(Continued)

FOREIGN PATENT DOCUMENTS

| WO | WO-2013016590 A1 * | 1/2013 | ............ A61B 18/04 |

*Primary Examiner* — Michael F Peffley
*Assistant Examiner* — Samantha M Good
(74) *Attorney, Agent, or Firm* — Seager, Tufte & Wickhem, LLP (57) ABSTRACT In one aspect, the present disclosure is directed to methods of treating various conditions including bladder conditions in a patient, comprising: positioning at least one ablative element of an ablative device on or over an adventitial surface of the bladder; and using the ablative device to denervate bladder nerve fibers. Other aspects of the present disclosure pertain, for example, to devices and kits for of treating bladder conditions.

20 Claims, 5 Drawing Sheets (56) References Cited

U.S. PATENT DOCUMENTS

2014/0039356 A1* 2/2014 Sachs ................ A61B 18/1815
607/101

* cited by examiner

BLADDER TREATMENT BY ABLATIVE DENERVATION

RELATED APPLICATION

This application is a continuation of Ser. No. 14/815,392, filed Jul. 31, 2015, and published on Feb. 4, 2016, under United States Publication No. 2016/0030107, which application claims the benefit of provisional application Ser. No. 62/031,584, filed Jul. 31, 2014, and titled "BLADDER TREATMENT BY ABLATIVE DENERVATION", which applications are hereby incorporated herein by reference in their entireties.

FIELD OF THE DISCLOSURE

The present disclosure relates to medical systems, compositions, devices, kits, and methods for treating various disorders including disorders of the urinary bladder.

BACKGROUND OF THE DISCLOSURE

Tissue ablation is a known technique for the treatment of various bodily disorders. Currently, ablation is used to eliminate pathological tissue (e.g., ablation of tumors or skin lesions), to remodel physical structures of tissue (e.g., ablation of hypertrophied prostate to alleviate obstruction of urine outflow), to address hyperactive function (e.g., local kidney nerve denervation to reduce blood pressure), and to modify the electrical conductivity of tissue (such as in treating cardiac arrhythmia).

Overactive bladder is a subjective, symptom-based syndrome affecting an estimated combined 11.8% of men and women in Europe. There is no specific pathologic or morphologic correlation and diagnosis is usually clinical and based on exclusion. Mainstay treatment today is a combination of pharmacologic treatment (e.g., using anticholinergics to block nerve signals related to bladder muscle contraction), behavior modification (e.g., bladder training, pelvic floor exercises, etc.), and potentially surgery (e.g., bladder augmentation, implantation of a bladder pacemaker, and bladder denervation, which typically involves cutting or excising part of a nerve). Injections of Botulinum toxin and sacral nerve stimulation are also considered as an intermediate between conservative medical and more radical surgical options.

In the present disclosure, tissue ablation, specifically, ablation of nerve fibers, is used to treat various disorders, including overactive bladder.

SUMMARY OF THE DISCLOSURE

The present disclosure is directed to improvements in the treatment of various disorders including bladder disorders.

In some aspects, the present disclosure is directed to methods of treating bladder conditions in a patient, comprising: positioning at least one ablative element of an ablative device on or over an adventitial surface of the bladder and using the ablative device to injure bladder nerve fibers causing denervation.

"Denervation" is defined herein as partially or totally blocking nerve conduction.

In certain embodiments, the bladder condition is bladder overactivity.

In certain embodiments, which may be used in combination with any of the above aspects and embodiments, the at least one ablative element is advanced through a urethra of the patient, into the bladder of the patent, and through an opening in a wall of the bladder.

In certain embodiments, which may be used in combination with any of the above aspects and embodiments, the at least one ablative element delivers an ablative chemical in an amount sufficient to denervate bladder nerve fibers, or creates ablative cryogenic temperatures that are sufficiently low to denervate bladder nerve fibers, or delivers ablative energy in an amount sufficient to denervate bladder nerve fibers.

In certain embodiments, which may be used in combination with any of the above aspects and embodiments, the denervated bladder nerve fibers are within 500 microns of the adventitial surface of the bladder.

In certain embodiments, which may be used in combination with any of the above aspects and embodiments, bladder nerve fibers are denervated in an area corresponding to 0.2 $cm^2$ to 5 $cm^2$ of the adventitial surface of the bladder.

In certain embodiments, which may be used in combination with any of the above aspects and embodiments, detrusor muscle function is not impaired.

In certain embodiments, which may be used in combination with any of the above aspects and embodiments, at least one of radio frequency (RF) energy, microwave energy, light energy, ultrasound energy, or electrocautery energy is delivered to the bladder.

In certain embodiments, which may be used in combination with any of the above aspects and embodiments, the at least one ablative element may comprise two or more electrodes in an array and RF energy is delivered to bladder tissue through the electrodes. In specific embodiments, the electrodes deliver RF energy in a bipolar mode of operation and/or the electrodes are penetrating electrodes having tips that are positioned in the bladder adventitia during energy delivery.

Other aspects of the disclosure pertain to ablative devices for treating a bladder condition. The devices comprise an elongate shaft and a deployable energy delivery mechanism or chemical delivery mechanism disposed at or near an end of the elongate shaft. The elongate shaft and energy delivery mechanism or chemical delivery mechanism are configured such that the energy delivery mechanism or chemical delivery mechanism can be advanced through a human urethra, into a human bladder and through an opening (e.g., an incision, puncture, etc.) in the wall of the bladder in a laterally contracted state, deployed to a laterally expanded state on the exterior of the bladder (after being advanced through the bladder wall), optionally retracted slightly and brought into contact with the adventitial surface of the bladder (as desired or required), activated such that treatment is delivered, returned to a laterally contracted state after treatment, and withdrawn back through the bladder wall, bladder and urethra. The devices have a width in the laterally expanded state that is larger than the width in the laterally contracted state, for example, having a width in the laterally expanded state that is at least 1.5 times, at least 2 times, at least 5 times, at least 10 times (or more) the width of the devices in the laterally contracted state.

In certain embodiments, which may be used in combination with any of the above aspects and embodiments, the device also has the capability to form an opening to create a space for the energy delivery mechanism or chemical delivery mechanism to achieve proximity to the nerves.

In certain embodiments, which may be used in combination with any of the above aspects and embodiments, the energy delivery mechanism is an electrode array. In this regard, the ablative devices may comprise: an elongate shaft and a deployable electrode array disposed proximal (i.e., at or near) an end of the elongate shaft, wherein the elongate shaft and deployable electrode array are configured such that the deployable electrode array can be (i) advanced in a laterally contracted state through a human urethra, into a human bladder and through an opening in a wall of the bladder (e.g., having a diameter that is smaller than an inside diameter of a human urethra, having sufficient flexibility to be advanced through the urethra, and optionally having a distal end that is sufficiently sharp to penetrate the wall of the bladder for instance, a sharp point and/or blade), (ii) deployed to a laterally expanded state after being advanced through the bladder wall (e.g., by expanding, inflating or allowing a shape memory effect to bend one or more members supporting the electrode array), (iii) brought into contact with an adventitial surface of the bladder for treatment (e.g., by retracting the laterally expanded electrode array by pulling back on the elongate shaft and, in certain embodiments, causing sharpened electrode tips to penetrate the adventitial surface of the bladder), (iv) returned to a laterally contracted state after treatment (e.g., by collapsing, deflating or straightening one or more members supporting the electrode array), and (v) withdrawn through the bladder wall, bladder and urethra.

In certain embodiments, which may be used in combination with any of the above aspects and embodiments, each electrode is deployed on a physically collapsible element.

In certain embodiments, which may be used in combination with any of the above aspects and embodiments, each electrode is deployed on a shape memory element.

In certain embodiments, which may be used in combination with any of the above aspects and embodiments, each electrode is deployed on an inflatable element.

In certain embodiments, which may be used in combination with any of the above aspects and embodiments, electrodes in the array are deployed on one or more linear or curvilinear elements.

In certain embodiments, which may be used in combination with any of the above aspects and embodiments, the array ranges from 0.5 cm to 2.5 cm across.

In certain embodiments, which may be used in combination with any of the above aspects and embodiments, the electrodes form a linear array or a polygonal array.

In certain embodiments, which may be used in combination with any of the above aspects and embodiments, the ablative device comprises a dissecting element (e.g., blade, puncturing tip, etc.).

In certain embodiments, which may be used in combination with any of the above aspects and embodiments, the ablative device comprises an RF generator.

Still other aspects of the disclosure pertain to kits that comprise two or more of the following components in any combination: (a) an ablative device in accordance with any of the above aspects and embodiments; (b) a tubular device that is configured for advancement through a subject's urethra, into a subject's bladder and optionally through an opening in a wall of the bladder, wherein the ablative device is configured to be advanced through the tubular device, (c) a dissecting element (e.g., a blade, puncturing tip, etc.); (d) a fluorescent dye that has selectivity for myelin (e.g., nerve fibers may be mapped by injecting such a dye into the lumbar spine epidural space); (e) a lubricant (e.g., a lubricity enhancing substance to assist with medical device insertion and withdrawal); and (f) an anesthetic (e.g., to prevent patient discomfort from a procedure performed with the kit). In some embodiments, the kits may comprise two of the components (a)-(f) in any combination. In some embodiments, the kits may comprise three of the components (a)-(f) in any combination. In some embodiments, the kits may comprise four of the components (a)-(f) in any combination. In some embodiments, the kits may comprise five of the components (a)-(f) in any combination. In some embodiments, the kits may comprise all of the components (a)-(f).

The devices, compositions, kits and methods described herein are advantageous, for example, in that they can be used in the treatment of conditions involving nerve fibers, for instance, any organ or tissue that is accessible through a body orifice, which can be punctured to establish proximity to nerve fibers. In the case of the bladder, the treatment site is accessible via the urethra and nerve fibers may be denervated in the adventitia without inflicting substantial damage to portions of the bladder wall beyond the adventitia, such as the bladder detrussor muscle, submucosa, mucosa, and urothelium.

These and other aspects, embodiments and advantages of the present disclosure will become apparent to those of ordinary skill in the art upon review of the detailed description set forth below.

DETAILED DESCRIPTION

A more complete understanding of the present disclosure is available by reference to the following detailed description of numerous aspects and embodiments of the disclosure. The detailed description which follows is intended to illustrate but not limit the invention.

The present disclosure pertains to methods, compositions, devices and kits that are useful in the treatment of organ conditions involving nerve fibers, for instance, any organ that is accessible through a body orifice, which can be punctured to establish proximity to nerve fibers, including the bladder, liver, kidney, uterus, and so forth. In certain embodiments, the present disclosure pertains to methods, compositions, devices and kits that are useful in the treatment of overactive bladder or endometriosis, among various other conditions.

In various embodiments, bladder nerve function is modulated by delivery of an ablative chemical in an amount sufficient to denervate bladder nerve fibers, by the creation of ablative cryogenic temperatures that are sufficiently low to denervate bladder nerve fibers, or by the delivery of ablative energy in an amount sufficient to denervate bladder nerve fibers, for instance, by delivering energy selected from one or more of radio frequency (RF) energy, microwave energy, light energy, ultrasound energy, or electrocautery energy to the adventitia of the bladder.

In certain beneficial embodiments, bladder nerve function is modulated by delivering thermal energy to nerve fibers proximal to the adventitial surface of the bladder, for example, primarily nerve fibers within the adventitia. In certain embodiments, all of the injured bladder nerve fibers may be localized within the adventitia. This is advantageous, for example, where it is desired to minimize or avoid impairment of detrusor muscle function or damage to the mucosa or other portions of the bladder.

Figure 1A:
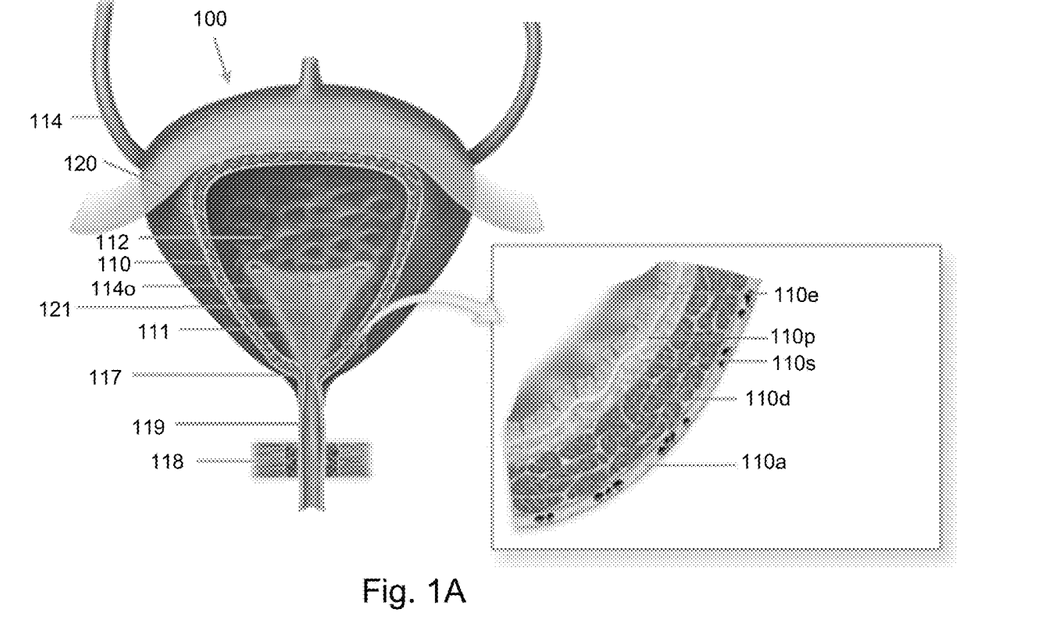
FIG. 1A is a schematic illustration of a human bladder and associated structures, and includes an expanded view of a portion of the bladder wall.

In this regard, and referring to FIG. 1, a human female bladder 100 and associated structures are shown, including the bladder wall 110, internal surface 112, trigone area 121, peritoneum 120, ureters 114, ureteral openings 114o, urethra 119, bladder neck 111, internal urethral sphincter 117, and external urethral sphincter 118. An expanded view of the bladder wall 100 is shown and it includes the mucosa, which includes transitional epithelium 110e and lamina propria 110p, submucosa 110s, detrusor muscle 110d and adventia 110a.

Complex innervation of the bladder wall includes nerve fibers penetrating from the exterior vesical plexus into various levels of the bladder wall all the way to the mucosa. Fibers ramify and branch as they extend from the exterior (adventitial) surface of the bladder.

Ganong's classic textbook, Review of Medical Physiology, 23rd edition, copyright© 2010 by The McGraw-Hill Companies, Inc., ISBN: 978-0-07-160568-7, MHID: 0-07-160568-1, describes bladder function in Chapter VIII on pp. 668. Briefly, the smooth muscle of the bladder wall, is arranged in spiral, longitudinal, and circular bundles. Contraction of the circular muscle, which is called the detrusor muscle, is mainly responsible for emptying the bladder during urination. These smooth muscle cell bundles are not under voluntary control. Farther along the urethra is a sphincter of skeletal muscle cells which are under voluntary control, and is termed the sphincter of the membranous urethra (or external urethral sphincter).

Figure 1B:
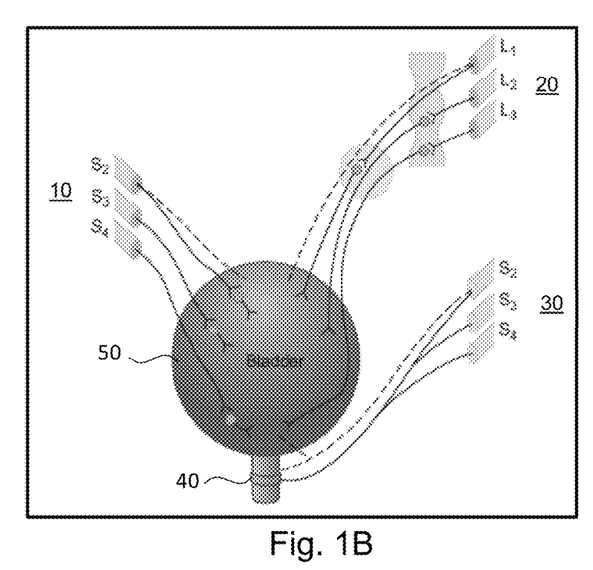
FIG. 1B is a schematic illustration of the neurologic innervation of the bladder.

The neurologic innervation of the bladder is shown schematically in FIG. 1B. The physiology of bladder emptying and the physiologic basis of its disorders remain under scientific study. Micturition is fundamentally a spinal reflex action (involuntary) facilitated and inhibited by higher brain centers subject to voluntary control. FIG. 1B shows the parasympathetic nerves 10 that leave the spinal column at the lowest parts of the spinal column from the sacrum between levels S2, S3 and S4. These "pelvic nerves" travel all the way to the outer surface of the bladder wall 50 where they synapse with clustered groups of neuronal cells called ganglion. Then, a second very short nerve leaves the ganglion diving into the bladder wall 50 and synapsing at a receptor. The "hypogastric nerves" 20 are sympathetic nerve fibers and thus leave the spinal column at a higher level up in the lumbar spine between vertebra L1, L2 and L3. They first synapse in ganglion far away from the bladder. Then a second long nerve fiber (axon) leaves the ganglion as the hypogastric nerves and directly enter the bladder wall 50. The third major group of nerves 30 going to the bladder/urethra are somatic (controlling skeletal muscle) and leave the spinal cord at the sacrum also between vertebra S2, S3 and S4.

During micturition, the perineal skeletal muscles and external urethral sphincter skeletal muscles are relaxed, the detrusor smooth muscle contracts, and urine passes out through the urethra. The bladder smooth muscle has some inherent contractile activity; however, when its nerve supply is intact, stretch receptors in the bladder wall initiate a reflex contraction that has a lower threshold than the inherent contractile response of the muscle. Fibers in the pelvic nerves are the afferent limb of the voiding reflex, and the parasympathetic fibers to the bladder that constitute the efferent limb also travel in these nerves. The reflex is integrated in the sacral portion of the spinal cord. These parasympathetic fibers are believed to be the nerve fibers and ganglion cells that are most impacted by methods described herein. The sympathetic nerves to the bladder from the hypogastric plexus play no part in micturition. The fact that these are post ganglionic fibers suggests that they may actually resprout from the distant ganglion and re-innervate post treatment thus restoring any function lost (in males they play a role in keeping ejaculate from entering the bladder).

In certain embodiments of the present disclosure, thermal energy is concentrated in nerve fibers proximal to the adventitial surface of the bladder, for instance, not penetrating more than about 250 to 500 microns from the adventitial surface in some embodiments, so as to prevent or avoid significant damage to the detrusor muscle. In various embodiments, the target nerve tissue population are the afferent and efferent nerve fibers.

In certain embodiments, the at least one ablative element is advanced through a urethra of the patient, into the bladder of the patent, and through an opening in the bladder wall. The bladder wall histology, the low/no pressurized viscus of the bladder itself and the free space with limited numbers of closely adjoined anatomically critical structures in the lower pelvis make this approach particularly appealing.

Ablative energy may be delivered by various energy delivery systems including systems that induce hyperthermia sufficient to denervate bladder nerve fibers disposed within the treated tissue, for example, monopolar or bipolar radio frequency (RF) systems, including pulsed radiofrequency systems, electrocautery systems, microwave systems, high intensity ultrasound systems, plasma generating systems, and laser systems (e.g., where laser energy is delivered directly from a laser or via a fiber optic element), among others, as well as systems that concentrate mechanical energy, such as extracorporeal shockwaves, cavitation or vibration, in an amount sufficient to injure bladder nerve fibers causing a functional denervation.

In certain embodiments, energy is delivered by systems wherein energy can be controlled depth-wise to ensure that the treatment does not cause substantial damage to portions of the bladder wall beyond the adventitia, including and preserving the bladder detrussor muscle, submucosa or mucosa, and urothelium.

In various embodiments, one or more suitable energy delivery components (e.g., selected from RF electrodes, ultrasound transducers, microwave antennas, lasers, etc.) is advanced through a patient's urethra, into the bladder and through an opening formed in the bladder wall such that energy can be delivered from the energy delivery component to tissue at or near the adventitial surface of the bladder. In other embodiments, the adventitial surface of the bladder may be accessed laparoscopically (e.g., through a laparoscope), via open abdominal surgery (e.g., via laparotomy) or, in the case of a female patient, transvaginally (i.e., through a vaginal incision).

Various embodiments will now be discussed in which radiofrequency (RF) delivery systems are employed. It should be recognized, however, that the present disclosure is not limited to such systems, and energy delivery may be accomplished by any of a variety of modalities, including those discussed above, among others.

As will be understood by those of ordinary skill in the art, RF energy delivery has practical advantages of being relatively inexpensive, with low cost generators readily commercially available. In addition, materials used to manufacture RF electrodes are relatively low cost and suitable for disposable devices. RF electrodes also tend to generate a high energy density, and therefore heat, immediately near the electrode tips, with energy density falling off quickly with distance. Accordingly, RF electrodes may be used to ablate a readily definable zone proximate the exterior surface of the bladder wall.

Bipolar RF ablation is particularly useful for targeted ablation, as bipolar RF electrodes may be used to achieve highly localized ablation in the region between the electrodes, with little or no current spreading elsewhere in the body. Bipolar RF ablation can also obviate the need for a separate grounding plate and risks from inadequately placed or missing grounding plates, such as skin burns, etc.

Figure 2A:
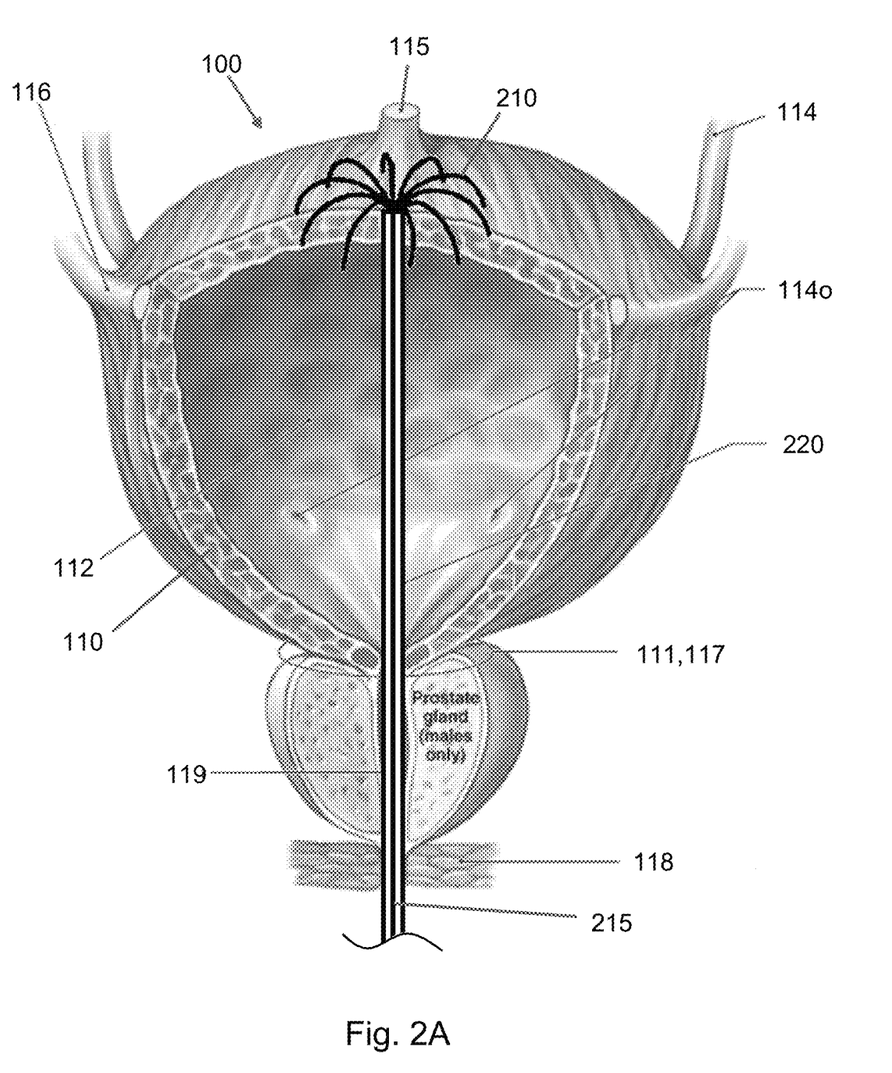
FIGS. 2A and 2B are schematic illustrations of a method of injuring bladder nerve fibers in differing portions of a human bladder, in accordance with an embodiment of the disclosure.

Turning now to FIG. 2A, a human male subject's bladder 100 and associated structures are shown, including the bladder wall 110, internal bladder surface 112, ureters 114, ureteral openings 1140, middle umbilical ligament 115, lateral umbilical ligaments 116, urethra 119, bladder neck 111, internal urethral sphincter 117, and external urethral sphincter 118. In the embodiment shown a tubular medical device 220 (e.g., a catheter, such as a "Stiletto-type" puncture-penetration catheter, a needle, a cannula, a scope, etc.) is advanced through the subject's urethra 119, into the bladder 100 and used to create a transmural tract through the bladder wall 110. The tubular medical device may vary in width (e.g., diameter), typically ranging from 5 french to 18 french, for example, ranging from 5 to 6 to 7 to 8 to 9 to 10 to 11 to 12 to 13 to 14 to 15 to 16 to 17 to 18 french (i.e., ranging between any two of the preceding numerical values). The width selected may be sufficiently small such that the opening in the bladder wall will be self-sealing. The opening may be formed, for example, by a sharpened tip of the tubular device 220 or by a previously inserted instrument that is used to pierce the bladder wall 110. In either case, it may be desirable to provide the penetrating element with a stop mechanism to prevent the penetrating element from extending significantly beyond adventitial surface of the bladder, so as to prevent the penetrating element from injuring nearby tissue (e.g., the uterus, etc.). An energy delivery component, specifically, an umbrella shaped RF electrode array 210 is inserted through the tubular device 220 via an elongate shaft 215. Upon emerging from the distal end of the tubular device 220, the electrodes of the electrode array are deployed (e.g., by a shape memory effect or other suitable deployment mechanism) and then pulled back into contact with the adventitial surface of the bladder wall. In certain embodiments, the electrodes have sharpened tips such that the electrode tips penetrate the adventitia. Upon being properly positioned, RF energy is directed from the electrodes into the bladder tissue, denervating tissue around and between the electrodes. The umbrella shaped RF electrode array 210 is then disengaged from tissue and withdrawn into the tubular device 220.

In certain embodiments, a width of the electrode array when deployed may range, for example, from 0.5 cm to 2.5 cm in greatest dimension, among other values, for example ranging from 0.5 cm to 1 cm to 1.5 cm to 2 cm to 2.5 cm (i.e., ranging between any two of the preceding numerical values). In the embodiment shown, the electrodes form a polygonal array (in particular, a regular polygonal array and, more particularly, a decagonal array). Although 10 electrodes are shown, other numbers of electrodes (e.g., 1, 2, 3, 4, 5, 6, 7, 8, 9, 11, 12, 13, 14, etc.) may be employed.

In certain embodiments, multiple microelectrodes are employed penetrate the bladder wall in a specified array and to a specified depth, followed by ablation at that depth.

Figure 3:
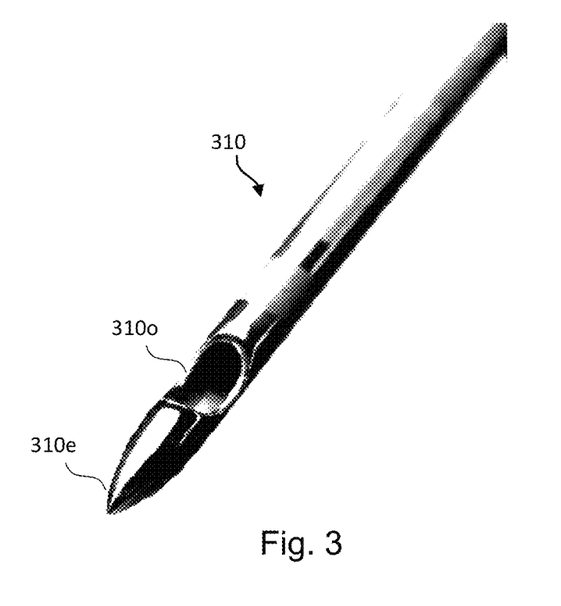
FIG. 3 is a schematic illustration of a needle which has a closed end and an opening on its side, which may be utilized in certain embodiments of the disclosure.

In certain embodiments, the tubular medical device through which the electrode array is delivered is a cannula or needle 310, which has a closed end 310e and an opening 310o on its side as shown in FIG. 3. A cannula or needle may contain, for example, a circular cross section or an elliptical cross section, among other possibilities.

Figure 2B:
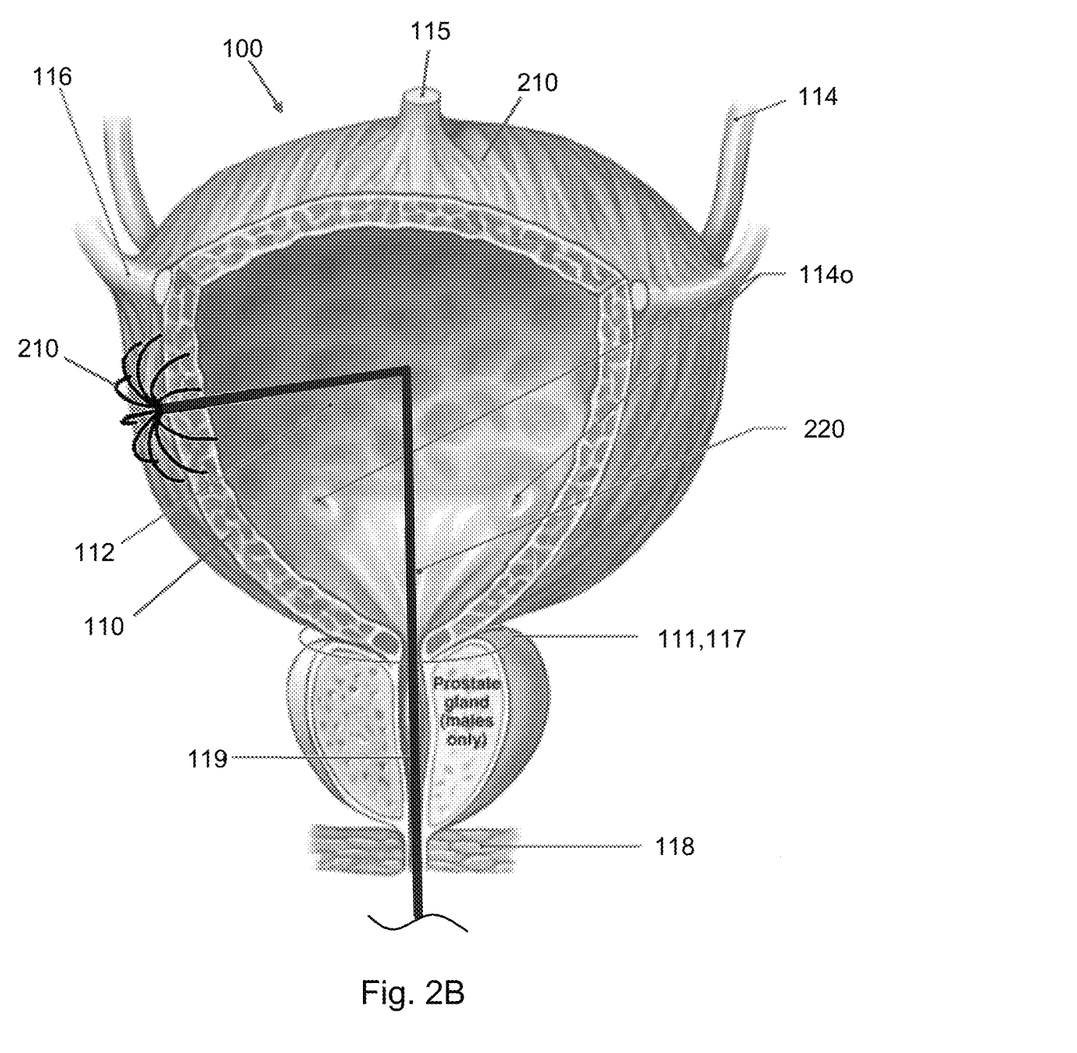

In the embodiment shown in FIG. 2A, the electrode array is deployed and the bladder tissue treated above the peritoneal reflection line (see numeral 120 in FIG. 1). The electrode array, however, can be deployed in a wide range of locations along the adventitial surface of the bladder. For example, the electrode array 210 may be delivered at a more acute angle (approaching 90 degrees) and deployed, and the bladder tissue treated, below the peritoneum as shown in FIG. 2B or in many other locations, as desired. Staying below the pelvis pain line (i.e., below the peritoneum) may increase safety and comfort.

Figure 4:
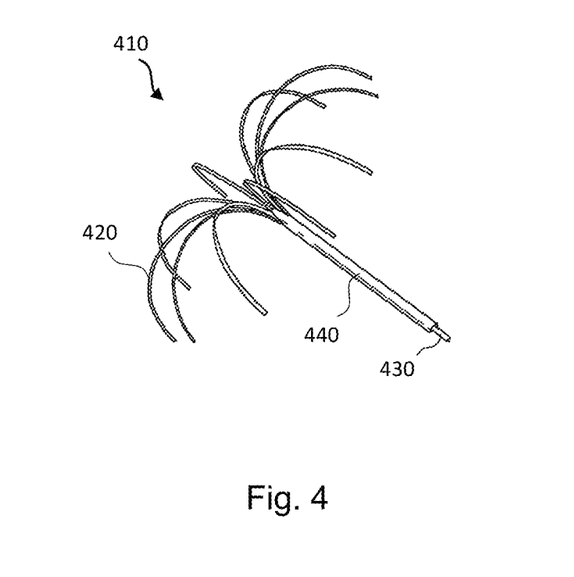
FIG. 4 is a schematic illustration of an ablative mechanism, which may be used in certain embodiments of the disclosure.

Referring to FIG. 4, the electrode elements of the electrode array 410 may be in the form of tines 420 that are secured (e.g., fixedly coupled by solder, weld, etc.) about the circumference of an elongate shaft 430 seated coaxially within a lumen of a tubular medical device 440 (e.g., catheter, needle, cannula, scope, etc.). Wires (not shown) run through the elongate shaft 430 to provide a suitable electrical potential to each of the electrodes. The electrode tines 420 may be formed of a substantially flat wire, each having a tissue piercing tip for easy tracking through solid tissue. The electrodes tines may be covered in insulation (for example a thin silicone sheet) by bridging between arrays and over the non-bladder contacting surface, except for at the tips of the electrode tines (not shown), which may also serve as a stop (e.g., arising from an abrupt increase in cross-sectional where the insulation terminates) to limit the depth that the electrode tines pierce the tissue. The tines 420 may be made of a shape-memory stainless steel or nitinol, and are sufficiently flexible to take on a substantially linear shape when constrained in the tubular medical device 440 lumen, and an outwardly curved shape due to shape memory when pushed outside of the tubular medical device 440 lumen. An output of an RF generator (not shown) is electrically coupled to the electrode tines 420, such that an RF signal applied from the generator output is transmitted to the electrode tines 420, and to tissue in which the electrode tines are deployed. For example, the RF signal may result in a series of alternating bipolar electrode elements around the electrode array perimeter, in which case an even number of electrode elements may be desirable (10 electrodes are shown, however 2, 4, 6, 8, 12, 14, etc. electrodes may be employed as well). Subsequent to treatment, the electrode array is pushed outward to disengage the tissue and withdraw back into the tubular medical device.

In other embodiments a deployment scheme analogous to that employed in umbrellas and parasols may be employed, in which the electrodes are mechanically deployed outward to an expanded position when outside the cannula lumen, the electrode array may then be pulled back such that the electrodes penetrate the bladder tissue, after which an RF signal is transmitted to the electrodes. Subsequent to treatment, the electrode array is pushed outward to disengage the tissue and retracted to a collapsed position whereby the electrode array can be withdraw back into the tubular medical device. As in the prior paragraph, the electrodes may be covered in insulation, except for the tips of the electrode tines, which may also serve as a stop to limit the depth that the electrode tines pierce the tissue.

It should be kept in mind that, although electrode arrays are specifically illustrated herein, a single energy delivering element or an array of energy delivering elements other than (or in addition to) one or more electrodes may be employed (e.g., one or more laser-energy delivering components or other energy delivering elements). Moreover, a single cryogenic probe or an array of cryogenic probes may be employed, or a single chemical delivery element or an array chemical delivery elements (e.g., one or more hollow needles or other chemical delivery elements) may be employed, among other possibilities. For instance, in specific embodiments, rather than corresponding to electrode tines, elements 420 of FIG. 4 may correspond to laser-energy delivering optical fibers, to cryogenic probes, or to needle injection catheters, among many other possibilities.

Figure 5:
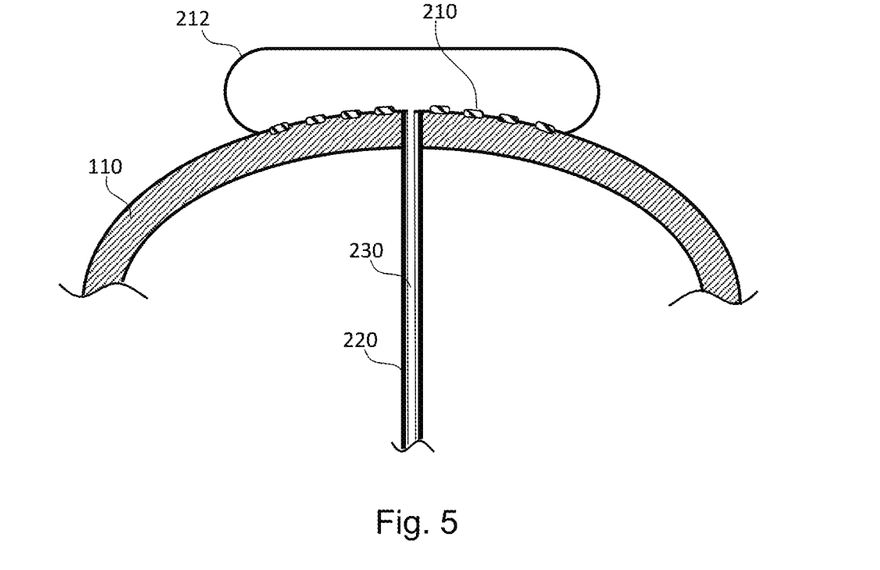
FIG. 5 is a schematic illustration of a method of injuring bladder nerve fibers in a portion of a human bladder, in accordance with an embodiment of the disclosure.

In other embodiments, and with reference to FIG. 5, a tubular medical device 220 (e.g., catheter, needle, cannula, scope, etc.) may be advanced through urethra, into the bladder and through an opening in the bladder wall 110. The opening may be formed, for example, by a sharpened tip of the tubular device 220 or by a previously inserted instrument that is used to pierce the bladder wall 110. An energy delivery component, specifically, an inflatable balloon 212 having an array of RF electrodes 210, which is attached to an elongate shaft 230 that comprises an inflation lumen for supplying and withdrawing an inflation fluid to and from the balloon 212 and wires (not shown) that run through the elongate shaft 230 to provide a suitable electrical potential to each of the electrodes in the array 210, is inserted through the tubular device 220 by pushing on the elongate shaft 230, thereby moving the balloon 212 through the tubular device 220. Upon emerging from the distal end of the tubular device 220, the balloon is inflated, thereby deploying the electrode array, which is then pulled back into contact with the adventitial surface of the bladder wall 110. At least a portion of the surface of the balloon may have a concave surface (e.g., analogous to a surface of a red blood cell), with the curvature of the concave surface of the balloon approximating the curvature of the convex surface of the bladder. In some embodiments, the electrodes 210 have sharpened tips (not shown) such that the electrode tips penetrate the adventitia. Upon being properly positioned, RF energy is directed from the electrodes 210 into the bladder tissue, denervating tissue around and between the electrodes. When treatment is complete, the balloon 212 is deflated and withdrawn into the tubular medical device 220, and the deflated balloon 212 and tubular device 220 are withdrawn from the patient. As elsewhere herein, the width of the tubular device 220 selected may be sufficiently small such that the wound will be self-sealing. In some embodiments, the electrode array 210 is introduced into and removed from the patient without the use of a tubular device 220.

Figure 6:
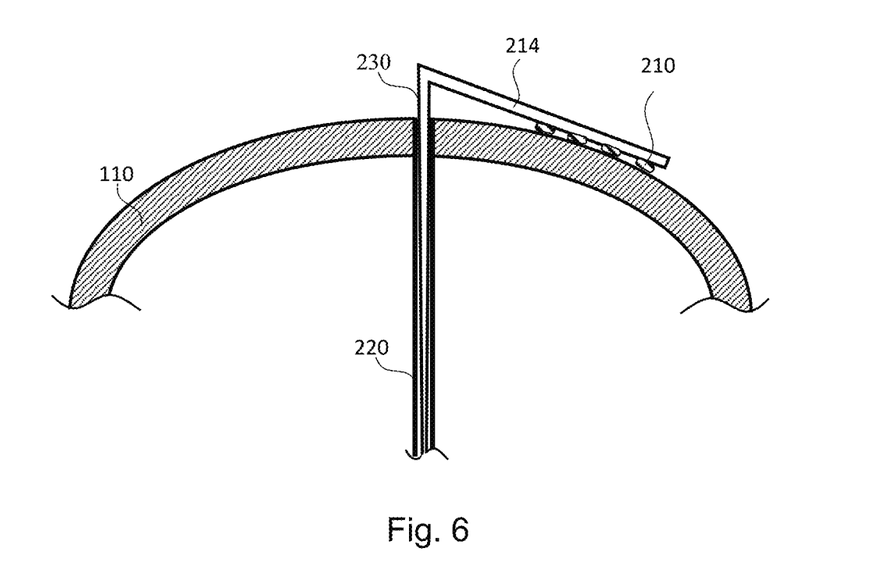
FIG. 6 is a schematic illustration of a method of injuring bladder nerve fibers in a portion of a human bladder, in accordance with another embodiment of the disclosure.

In still other embodiments, and with reference to FIG. 6, a tubular medical device 220 (e.g., catheter, needle, cannula, scope, etc.) is advanced through urethra, into the bladder and through an opening in the bladder wall 110 as previously described. An energy delivery component provided at an end of an elongate shaft 230, specifically, a collapsible hook 214 having an array of RF electrodes 210 that is operable between a collapsed and expanded position (e.g., via a spring-loaded hinge and pull cable) is inserted through the tubular device 220. Wires (not shown) run through the elongate shaft 230 to provide a suitable electrical potential to each of the electrodes in the array 210. Upon emerging from the distal end of the tubular medical device 220, the 214 hook is expanded, thereby deploying the electrode array, and is then pulled back into contact with the adventitial surface of the bladder wall 110. In some embodiments, the electrodes have sharpened tips (not shown) such that the electrode tips penetrate the adventitia. Upon being properly positioned RF energy is directed from the electrodes 210 into the bladder tissue, denervating tissue around and between the electrodes. If desired, the hook may be rotated to direct RF energy to other portions of the bladder tissue. Typical overall lengths for the electrode array may range, for example, from 0.5 cm to 2.5 cm, among other possible values. When treatment is complete, the hook 214 is collapsed and withdrawn into the tubular medical device 220, and the hook 214 and tubular medical device 220 are withdrawn from the patient. As elsewhere herein, the width of the tubular medical device 220 selected may be sufficiently small such that the wound will be self-sealing.

In the female anatomy, the uterus lies proximate to the bladder, in which it case may be desirable to create a zone of separation between the deployed ablative device and the uterus, for instance, using a fluid medium (e.g., a non-conductive gel) or solid medium (e.g., a balloon or shield at the end of the electrode array) to ensure that no harm to the uterus occurs. In certain embodiments, separation may be achieved or augmented by dissection.

In certain embodiments, treatment may be enhanced by mapping the location of the nerve fibers prior to tissue ablation. For example, nerve fibers may be mapped by injecting a suitable dye (e.g., a fluorescent dye that has selectivity for myelin such as FluoroMyelin™ Red or FluoroMyelin™ Green, Molecular Probes, Eugene, OR, among others) into the L3-L5 lumbar spine epidural space. In other embodiments, the nerves may be detected using a mapping catheter, such as the Boston Scientific Constellation® Full Contact Mapping Catheter, or similar product.

Other aspects of the disclosure relate to kits that are suitable for performing the procedures described herein. The kits may include, for example, any combination of two or more of the following: (a) a tubular medical device (e.g., a catheter, such as a "Stiletto-type" puncture-penetration catheter, a needle, a cannula, a scope, etc.) suitable for advancement through the subject's urethra, into the bladder and through an opening in the bladder wall, (b) a device having an electrode array at its distal end that is suitable for advancement through a tubular medical device (e.g., the device of component (a)), (c) lubricant, (d) an anesthetic, (e) a fluorescent dye that has selectivity for myelin, (f) a dissection component, (g) suitable packaging material, and (h) printed material with one or more of the following: (i) storage information and (ii) instructions regarding how use the kit to treat a subject.

Although various embodiments are specifically illustrated and described herein, it will be appreciated that modifications and variations of the present disclosure are covered by the above teachings and are within the purview of the appended claims without departing from the spirit and intended scope of the invention.

The invention claimed is:
1. A method of treating a bladder condition in a patient, comprising:

positioning at least one ablative element of an ablative device in contact with an adventitial surface of the bladder; and using the ablative device to deliver ablative energy to the adventitial surface of the bladder to denervate bladder nerve fibers.

2. The method of claim 1, wherein the at least one ablative element is advanced through a urethra of the patient, into the bladder of the patient, and through an opening in a wall of the bladder.

3. The method of claim 1, wherein the bladder condition is bladder overactivity.

4. The method of claim 1, wherein the at least one ablative element delivers an ablative chemical in an amount sufficient to denervate bladder nerve fibers or creates ablative cryogenic temperatures that are sufficiently low to denervate bladder nerve fibers.

5. The method of claim 1, wherein the at least one ablative element delivers ablative energy in an amount sufficient to denervate bladder nerve fibers.

6. The method of claim 5, wherein denervated bladder nerve fibers are within 500 microns of the adventitial surface of the bladder.

7. The method of claim 5, wherein the energy does not impair function of a detrusor muscle of the patient.

8. The method of claim 5, comprising delivering at least one of radio frequency (RF) energy, microwave energy, light energy, ultrasound energy, or electrocautery energy to the bladder.

9. The method of claim 8, wherein the at least one ablative element comprises two or more electrodes in an array and wherein RF energy is delivered to bladder tissue through the electrodes.

10. The method of claim 9, wherein the electrodes deliver RF energy in a bipolar mode of operation.

11. The method of claim 9, wherein the ablative device comprises penetrating electrodes having tips that are positioned in the adventitial surface of the bladder during energy delivery.

12. The method of claim 9, wherein bladder nerve fibers are denervated in an area corresponding to 0.2 cm$^2$ to 5 cm$^2$ of the adventitial surface of the bladder.

13. A method of treating a bladder condition in a patient, comprising:

positioning at least one ablative element of an ablative device in contact with an adventitial surface of the bladder by advancing the at least one ablative element through a urethra of the patient, into the bladder of the patient, and through an opening in a wall of the bladder;

delivering ablative energy from the at least one ablative element in an amount sufficient to denervate bladder nerve fibers within the adventitia of the bladder.

14. The method of claim 13, comprising delivering at least one of radio frequency (RF) energy, microwave energy, light energy, ultrasound energy, or electrocautery energy to the bladder.

15. The method of claim 13, wherein the at least one ablative element comprises two or more electrodes in an array and wherein ablative RF energy is delivered to bladder tissue through the electrodes.

16. A method of treating a bladder condition using an ablative device that comprises an elongate shaft and a deployable electrode array disposed proximate an end of the elongate shaft, the method comprising:

advancing the deployable electrode array in a laterally contracted state through a human urethra, into a human bladder and through an opening in a wall of the bladder:

deploying the deployable electrode array and bringing the electrode array into contact with an adventitial surface of the bladder for treatment;

using the ablative device to denervate bladder nerve fibers;

returning the deployable electrode array to a laterally contracted state; and withdrawing the ablative device through the bladder wall, bladder and urethra.

17. The method of claim 16, wherein each electrode of the deployable electrode array is deployed on a shape memory element.

18. The method of claim 16, wherein each electrode of the deployable electrode array is deployed on an inflatable element.

19. The method of claim 16, wherein the deployable electrode array ranges from 0.5 cm to 2.5 cm across when deployed.

20. The method of claim 16, wherein the bladder nerve fibers are ablated using an RF generator that is electrically coupled to the deployable electrode array.

* * * * *